(12) United States Patent
Yamada et al.

(10) Patent No.: US 11,519,797 B2
(45) Date of Patent: Dec. 6, 2022

(54) GRIPPING FORCE MEASUREMENT DEVICE

(71) Applicants: Kitagawa Industries Co., Ltd., Inazawa (JP); University of Yamanashi, Kofu (JP)

(72) Inventors: Kazuki Yamada, Kasugai (JP); Yasuo Kondo, Kasugai (JP); Lu Zhao, Kasugai (JP); Hidetsugu Terada, Kofu (JP); Koji Makino, Kofu (JP); Takaiki Kanagawa, Kofu (JP)

(73) Assignees: Kitagawa Industries Co., Ltd., Inazawa (JP); University of Yamanashi, Kofu (JP)

( * ) Notice: Subject to any disclaimer, the term of this patent is extended or adjusted under 35 U.S.C. 154(b) by 172 days.

(21) Appl. No.: 15/733,233

(22) PCT Filed: Dec. 28, 2018

(86) PCT No.: PCT/JP2018/048582
§ 371 (c)(1),
(2) Date: Jun. 13, 2020

(87) PCT Pub. No.: WO2019/132032
PCT Pub. Date: Jul. 4, 2019

(65) Prior Publication Data
US 2020/0386632 A1    Dec. 10, 2020

(30) Foreign Application Priority Data

Dec. 28, 2017 (JP) .............................. JP2017-254807

(51) Int. Cl.
*G01L 1/00* (2006.01)
*G01L 1/22* (2006.01)
(Continued)

(52) U.S. Cl.
CPC ................ *G01L 1/22* (2013.01); *A61B 5/225* (2013.01); *G01L 5/0028* (2013.01); *A61B 2562/0247* (2013.01)

(58) Field of Classification Search
CPC ......... G01L 1/22; G01L 5/0028; A61B 5/225; A61B 2562/0247
See application file for complete search history.

(56) References Cited

U.S. PATENT DOCUMENTS 5,152,296 A * 10/1992 Simons .............. A61B 5/02241
                                                             600/483
6,132,383 A * 10/2000 Chesney ................ A61B 5/022
                                                              73/866.5
(Continued)

FOREIGN PATENT DOCUMENTS

JP    1974-128350 U1    11/1974
JP    S49128350 U       11/1974
(Continued)

OTHER PUBLICATIONS

Japan Patent Office, Notice of Reasons for Refusal, dated Nov. 10, 2020 for Japanese patent application No. 2017-254807.
(Continued)

*Primary Examiner* — Max H Noori
(74) *Attorney, Agent, or Firm* — Wiggin and Dana LLP

(57) ABSTRACT

A gripping force measurement device includes a body portion and a plurality of pressure sensors. The plurality of pressure sensors includes at least one first sensor and two or more second sensors including pressure-sensitive surfaces oriented in the same direction. A pressure-sensitive surface of the first sensor and the pressure-sensitive surfaces of the two or more second sensors are disposed such that, when a subject pressurizes the pressure-sensitive surface of the first sensor and the pressure-sensitive surfaces of the two or more (Continued)

second sensors, the gripping force measurement device is grippable by the subject.

8 Claims, 13 Drawing Sheets

(51) Int. Cl.
    *A61B 5/22*           (2006.01)
    *G01L 5/00*           (2006.01)

(56) References Cited

U.S. PATENT DOCUMENTS

| | | | |
|---|---|---|---|
| 6,264,621 | B1 | 7/2001 | Paske |
| 6,454,681 | B1* | 9/2002 | Brassil .................. A63B 23/16 482/49 |
| 6,491,647 | B1* | 12/2002 | Bridger ................. G01L 1/2231 128/900 |
| 11,291,510 | B2* | 4/2022 | Shelton, IV ....... A61B 17/1155 |
| 11,295,846 | B2* | 4/2022 | Kamen ................. F04B 49/065 |
| 2003/0054923 | A1 | 3/2003 | Brassil et al. |
| 2004/0177686 | A1 | 9/2004 | Johansson |
| 2007/0119248 | A1 | 5/2007 | Lee |
| 2010/0106060 | A1 | 4/2010 | Tsuji |
| 2010/0160796 | A1* | 6/2010 | Banet ................. A61B 5/14551 600/509 |
| 2019/0056248 | A1* | 2/2019 | Shepherd ............. B25J 13/088 |
| 2019/0365493 | A1* | 12/2019 | Joseph ................... G06F 3/014 |
| 2021/0290080 | A1* | 9/2021 | Ahmed ................. G16H 10/60 |
| 2021/0369126 | A1* | 12/2021 | Khachaturian .... A61B 5/02225 |
| 2022/0108262 | A1* | 4/2022 | Celia .............. G06Q 10/063118 |

FOREIGN PATENT DOCUMENTS

| | | |
|---|---|---|
| JP | 2005503229 A | 2/2005 |
| JP | 2007167188 A | 2/2007 |
| JP | 2007-167188 A | 7/2007 |
| JP | 2010-99263 A | 5/2010 |
| JP | 201099263 A | 5/2010 |
| JP | 2017-127406 A | 7/2017 |
| JP | 2017127406 A | 7/2017 |
| KR | 20120008122 A | 1/2012 |
| KR | 20150072782 A | 6/2015 |
| WO | 2009/150417 A2 | 12/2009 |
| WO | 2009150417 A2 | 12/2009 |

OTHER PUBLICATIONS

European Patent Office, Extended European Search Report, dated Jul. 2, 2021 in corresponding European patent application No. 18897165.9.
Korean Office Action (Notification of Reason for Refusal), dated Jan. 13, 2022 in corresponding Korean patent application No. 10-2020-7017792.
Translation of International Search Report (Form PCT/ISA/210) for PCT/JP2018/048582, dated Mar. 19, 2019.
Written Opinion of the International Searching Authority (Form PCT/ISA/237) for or PCT/JP2018/048582, dated Mar. 19, 2019.
Notification of Transmittal of Translation of the International Preliminary Report on Patentability (form PCT/IB/338) for International Application No. PCT/JP2018/048582, dated Jul. 9, 2020.
PCT International Preliminary Report on Patentability (form PCT/IB373) for International Application No. PCT/JP2018/048582, dated Jun. 30, 2020.
English translation of Written Opinion of the International Searching Authority (form PCT/ISA/237) for International Application No. PCT/JP2018/048582, dated Mar. 19, 2019.
Chinese Patent Office (CNIPA), First Office Action, dated Sep. 20, 2022 in corresponding Chinese patent application No. 201880082058.1.

* cited by examiner

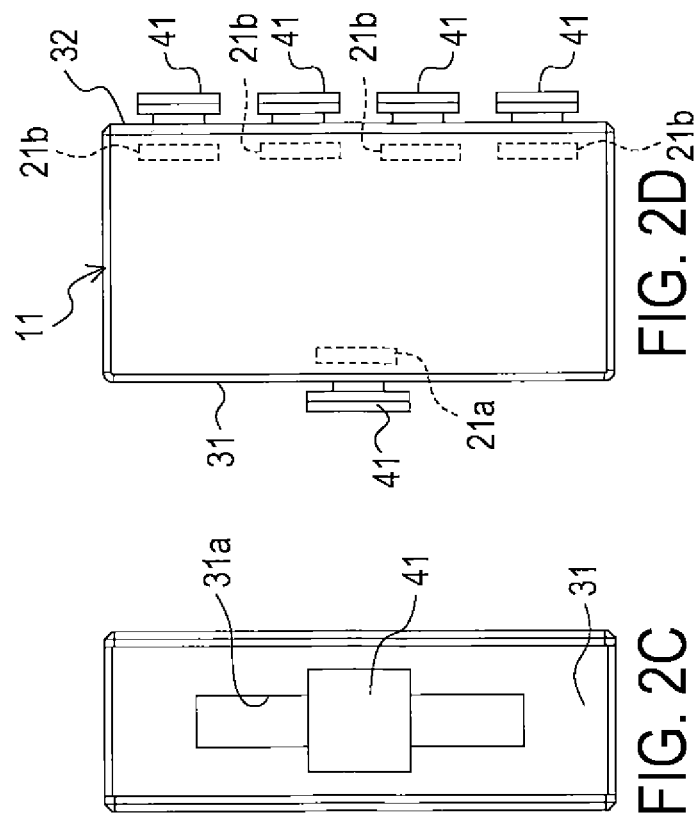
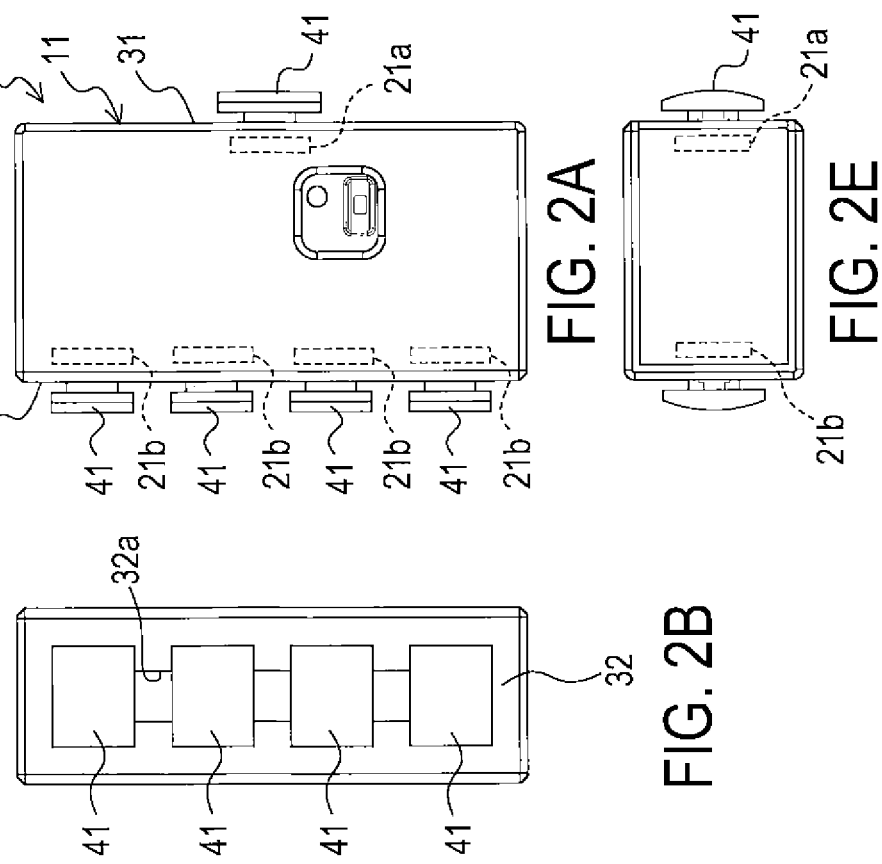

GRIPPING FORCE MEASUREMENT DEVICE

CROSS-REFERENCE TO RELATED APPLICATION

This international application claims the priority based on Japanese Patent Application No. 2017-254807, filed with the Japan Patent Office on Dec. 28, 2017, and the entire contents of Japanese Patent Application No. 2017-254807 are incorporated herein by reference.

TECHNICAL FIELD

The present disclosure relates to a device that measures hand force.

BACKGROUND ART

Conventionally, various devices that acquire information on the hand such as finger force have been proposed. A hand dynamometer is an example of such a device. Patent Document 1 proposes, in addition to the hand dynamometer, a device that measures multidirectional force applied by a hand to evaluate finger's dexterity and ability to manipulate an object.

CITATION LIST

Patent Literature

Patent Document 1: JP 2005-503229 T

SUMMARY OF INVENTION

Technical Problem

In a conventional device, it has been difficult to acquire detailed information on hand force, for example, which finger has weaker force than force of the other fingers.

One aspect of the present disclosure is desirably to propose a technique capable of acquiring detailed information on finger force.

Solution to Problem

One aspect of the present disclosure is a gripping force measurement device that measures gripping force of a subject, and includes a body portion and a plurality of pressure sensors held by the body portion. The plurality of pressure sensors include a first sensor that is at least one pressure sensor, and two or more second sensors other than the first sensor. The two or more second sensors include pressure-sensitive surfaces oriented in the same direction. A pressure-sensitive surface of the first sensor and the pressure-sensitive surfaces of the two or more second sensors are disposed such that, when a subject pressurizes the pressure-sensitive surface of the first sensor and the pressure-sensitive surfaces of the two or more second sensors, the gripping force measurement device is grippable by the subject.

According to such a configuration, since pressure can be acquired for each of the plurality of pressure sensors, more detailed information on finger force can be acquired, as compared to the case of measuring the overall gripping force of a hand. For example, the information on finger force can be acquired by bringing a thumb into contact with the first sensor and fingers other than the thumb into contact with the plurality of second sensors, respectively to apply force to sandwich the sensors.

Additionally, unlike the gripping force measurement device described above, in a gripping force measurement device that includes only a pair of pressure sensors pressurized by a thumb and other fingers, the following problems may arise. For example, a rotational moment may be generated in the gripping force measurement device depending on the positional relationship between a thumb and other fingers. As a result, not only that gripping force cannot be measured precisely, but also the gripping force measurement device itself may be difficult to grip. However, according to the gripping force measurement device of one aspect of the present disclosure described above, since two or more second sensors are provided, the device can be gripped with two or more fingers other than a thumb, and thus the problems described above is less likely to arise.

The "same direction" described herein for the two or more second sensors is not limited to the same direction in a strict sense, and is substantially the same direction in the range where the same effects as described above are achieved even with a small difference in the direction.

In the gripping force measurement device described above, the body portion may be configured to change a holding position of at least one of the first sensor and the two or more second sensors.

According to such a configuration, force can be measured appropriately by changing positions of the pressure-sensitive surfaces of the pressure sensors according to a subject's hand.

Additionally, the gripping force measurement device described above may further include a guide portion provided in the body portion, and configured to come into contact with a finger of the subject to guide a position of the finger with respect to the pressure-sensitive surface of at least one of the two or more second sensors.

According to such a configuration, since the finger of the subject can be brought into contact with an appropriate position, force measurement can be performed appropriately.

Additionally, in the gripping force measurement device described above, the body portion may include a plurality of buttons for pressurizing the plurality of pressure sensors. Additionally, among the plurality of buttons, a button for pressurizing the pressure-sensitive surface of the first sensor, and a button for pressurizing at least one of the pressure-sensitive surfaces of the two or more second sensors may protrude outward from the body portion.

According to such a configuration, when finger force is applied to the pressure-sensitive surface, a finger is less likely to come into contact with the body portion. Accordingly, a risk that finger force is applied to the body portion or that the pressure-sensitive surface of the pressure sensor is pressurized in an improper direction can be reduced, and force measurement can be performed appropriately.

Additionally, in the gripping force measurement device described above, the body portion may be configured such that a distance between the first sensor and the two or more second sensors is changeable.

According to such a configuration, a position of a button for pressurizing the pressure-sensitive surface of the pressure sensor can be changed according to the subject's hand, and force measurement can be performed appropriately.

BRIEF DESCRIPTION OF DRAWINGS

FIG. 2A is a right side view illustrating the gripping force measurement device in accordance with the first embodiment, FIG. 2B is a front view illustrating the gripping force measurement device, FIG. 2C is a rear view illustrating the gripping force measurement device, FIG. 2D is a left side view illustrating the gripping force measurement device, FIG. 2E is a bottom view illustrating the gripping force measurement device, and FIG. 2F is a plan view illustrating the gripping force measurement device.

LIST OF REFERENCE NUMERALS

Figure 1A:
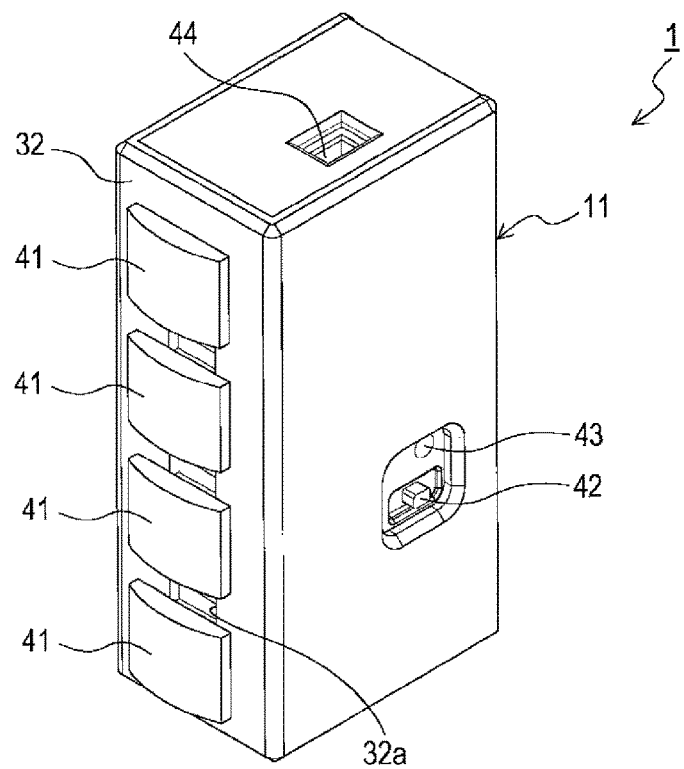
FIG. 1A is a perspective view illustrating a gripping force measurement device in accordance with a first embodiment.
Figure 1B:
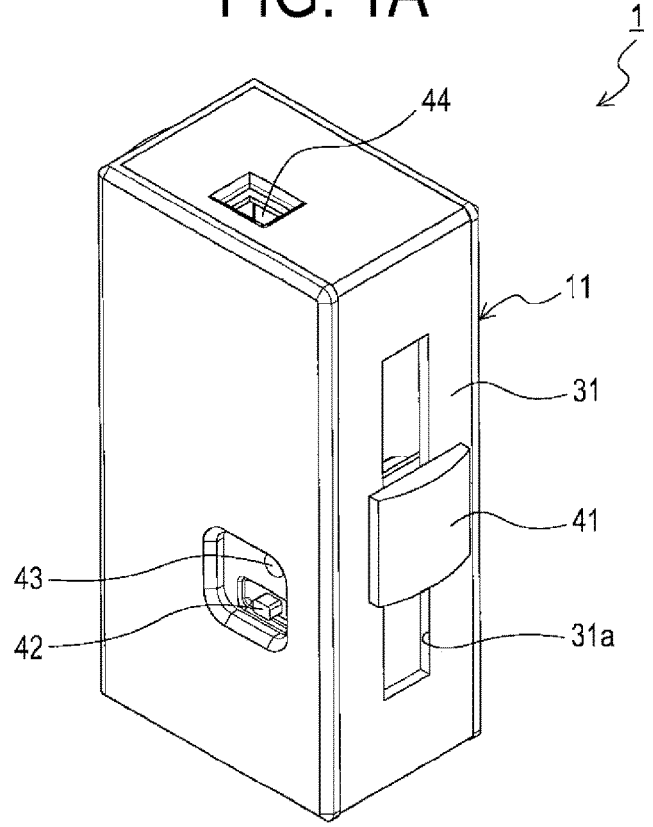
FIG. 1B is a perspective view illustrating the gripping force measurement device from a perspective that is different from that of FIG. 1A.

1: Gripping force measurement device, 11: Body portion, 21: Pressure sensor, 21a: First sensor, 21b: Second sensor, 23: Variable resistor, 24: Electrode, 31: First surface, 31a: Slit, 32: Second surface, 32a: Slit, 41: Button, 41a: Disc-shaped portion, 41b: Columnar portion, 41c: Contact portion, 42: Power button, 43: LED, 44: Connection interface, 51: Cable, 52: Installation surface, 61: Control and communication module, 62: Acquisition unit, 63: Communication unit, 64: Power supply unit, 65: Control unit, 66: CPU, 67: Memory, 68: Battery, 71: PC, 72: Reception module, 73: Display, 101: Gripping force measurement device, 110: Body portion, 111: First housing, 112: Second housing; 121: Change mechanism, 122: Female screw portion, 123: Male screw portion, 131: Guide portion, 141: Body portion, 142: Button, 151: Body portion, 152: Button, 161: Button, 162: Contact auxiliary portion, 171: Pressure sensor, 172: Housing

DESCRIPTION OF EMBODIMENTS

Embodiments of the present disclosure will be described below with reference to the drawings.

1. First Embodiment 1-1. Overall Configuration

As illustrated in FIGS. 1A and 1B and FIGS. 2A to 2F, a gripping force measurement device 1 that measures gripping force of a subject in accordance with a first embodiment includes a body portion 11 and a plurality of pressure sensors held by the body portion 11. The plurality of pressure sensors include a first sensor 21a that is one pressure sensor, and four second sensors 21b that are pressure sensors other than the first sensor. Note that, in a case where the first sensor 21a and the second sensors 21b are not differentiated, the first sensor 21a and the second sensors 21b may also be described as a pressure sensor 21. Note that in the first embodiment, the first sensor 21a corresponds to a first finger, and the four second sensors 21b correspond to second to fifth fingers.

The body portion 11 is a housing of a substantially rectangular parallelepiped shape. The body portion 11 holds, in addition to a plurality of the pressure sensors 21 described above, a plurality of buttons 41, a power button 42, an LED 43, a connection interface 44, and the like at positions along an outer surface. Additionally, the body portion 11 holds a control and communication module 61, a battery 68, and the like described below inside of the body portion 11.

1-2. Configuration of Pressure Sensor and Button

Since the first sensor 21a and the four second sensors 21b include the same configuration, a configuration of the first sensor 21a will be described and the description of the other sensors will be omitted.

Figure 3A:
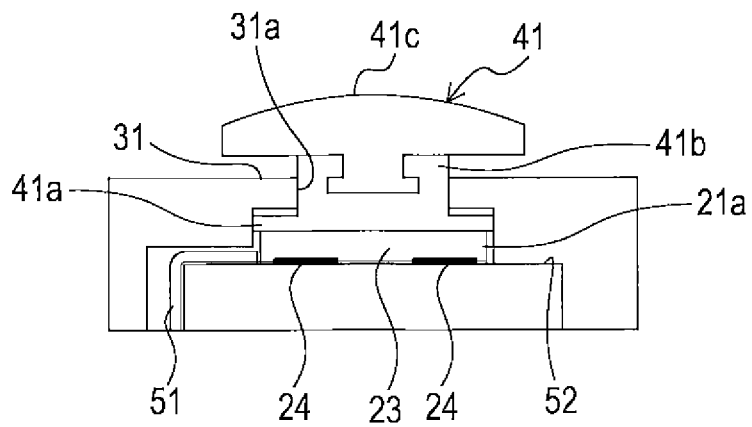
FIG. 3A is a cross-sectional view illustrating a pressure sensor and a button.
Figure 3B:
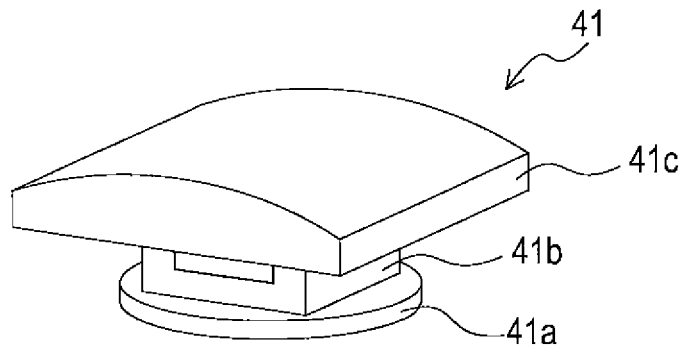
FIG. 3B is a perspective view illustrating the button.
Figure 3C:
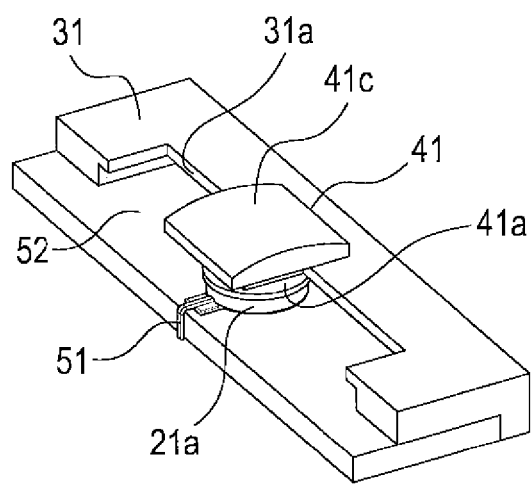
FIG. 3C is a partial perspective explanatory view illustrating arrangement of the pressure sensor and the button of a body portion.
Figure 4A:
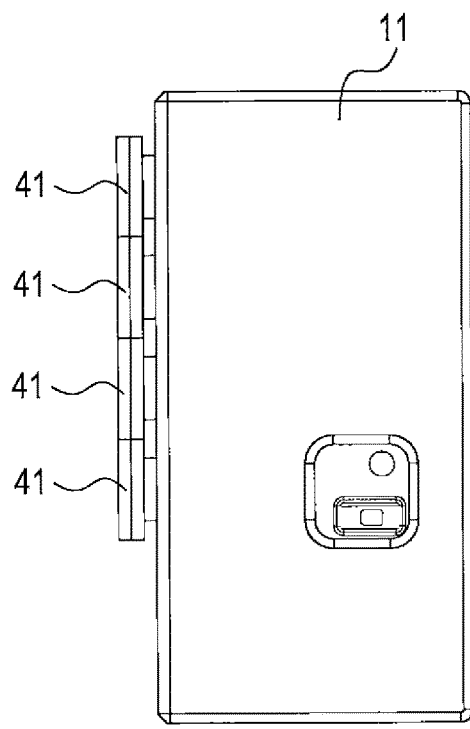
FIG. 4A is a plan view illustrating a state where a button is moved.
Figure 4B:
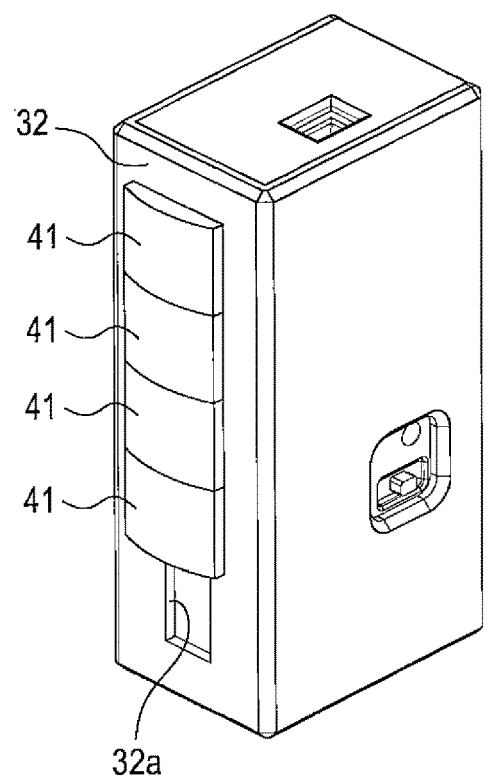
FIG. 4B is a perspective view illustrating that state.
Figure 4C:
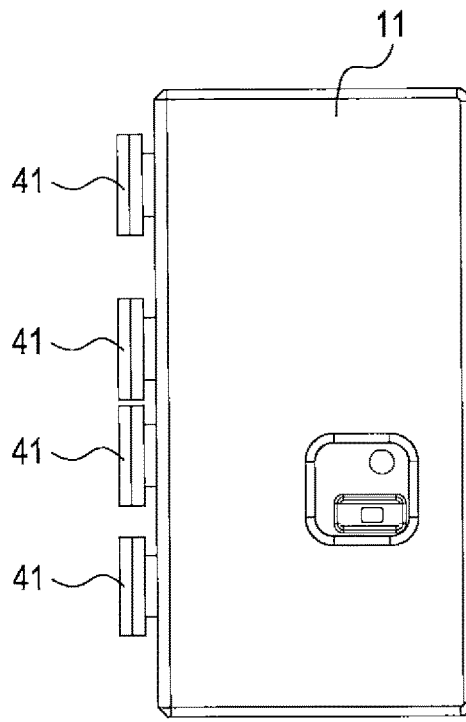
FIG. 4C is a plan view illustrating a state where a button is moved to another position.
Figure 4D:
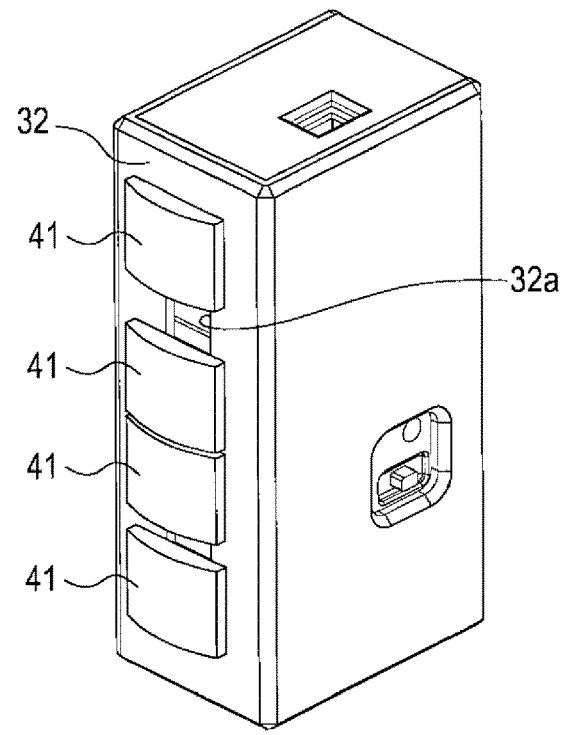
FIG. 4D is a perspective view illustrating that state.

As illustrated in FIGS. 3A and 3C, the first sensor 21a includes a variable resistor 23 and a plurality of electrodes 24 disposed below the variable resistor 23. The variable resistor 23 may be disc-shaped as viewed from the direction in which the button 41 is pressed (pressing direction). At least one of the plurality of electrodes 24 is used as a signal electrode, and at least another one of the plurality of electrodes 24 is used as a ground electrode. The variable resistor 23 is made from a conductive foam elastomer material having electrical conductivity imparted by dispersing conductive filler in an elastomer material and obtained by foaming the elastomer material. The variable resistor 23 is compressed according to pressure under pressurization, and as a compression amount of the variable resistor 23 increases, electric resistance of the variable resistor 23 decreases.

In the present embodiment, the variable resistor 23 is molded to have a thickness ranging from 1 mm to 10 mm and have electric resistance of $1 \times 10^3 \Omega$ or greater in a state of non-pressurization. In a state of pressurization, the variable resistor 23 is compressed to have a thickness 80% or less of the thickness obtained in a state of non-pressurization, and have electric resistance of $\frac{1}{500}$ to $\frac{1}{10}$ of the electric resistance obtained in a state of non-pressurization.

A cable 51 is connected to the plurality of electrodes 24. An electrical signal in response to electrical resistance is output to the control and communication module 61 via the cable 51, and output to an external device (PC 71 described below).

One button 41 corresponding to the first sensor 21a is attached to one surface of the first sensor 21a. The button 41 for the first sensor 21a is a button for pressurizing a pressure-sensitive surface of the first sensor 21a. The "pressure-sensitive surface" described herein refers to a surface in which the first sensor 21a is capable of detecting pressurizing force when the surface is pressurized. In the first embodiment, the "pressure-sensitive surface" refers to a surface of the variable resistor 23 having a disc shape in which the button 41 is provided. In the following description, the direction in which the pressure-sensitive surface faces is the normal direction of the pressure-sensitive surface.

Additionally, the button for pressurizing the pressure-sensitive surface is a button that serves as an auxiliary role for a subject to apply finger force to the pressure-sensitive surface. According to such a button, a contact surface that is a surface in which a finger applies force can be positioned away from the pressure-sensitive surface. Accordingly, a subject's erroneous operation of the gripping force measurement device 1 is suppressed and the operability of the gripping force measurement device 1 is improved.

As illustrated in FIGS. 3A and 3B, the button 41 is constituted by assembling two upper and lower members. The button 41 includes a disc-shaped portion 41a, a columnar portion 41b, and a contact portion 41c. The disc-shaped portion 41a has a circular shape having a larger diameter than a diameter of the first sensor 21a. The columnar portion 41b is a prism-shaped member extending from the disc-shaped portion 41a on the opposite side to the first sensor 21a. The contact portion 41c is a substantially plate-like member provided in an extended end of the columnar portion 41b.

The contact portion 41c has generally a plate-like shape, but a surface on the side of the columnar portion 41b has a planar shape, and an opposite surface of the columnar portion 41b has a protruding shape. Additionally, the opposite surface has a rounded shape, and more specifically, has a cylindrical shape divided by a surface along the axial direction.

1-3. Arrangement of Pressure Sensor

As illustrated in FIGS. 2A, 2D, and the like, the first sensor 21a is disposed near a first surface 31 of the body portion 11. Additionally, the four second sensors 21b are disposed near a second surface 32 provided on the opposite side to the first surface 31 of the body portion 11.

That is, the body portion 11 holds the first sensor 21a and the second sensors 21b such that the pressure-sensitive surface of the first sensor 21a and the pressure-sensitive surfaces of the four second sensors 21b are oriented in opposite directions. In other words, (i) the pressure-sensitive surfaces of the four second sensors 21b are oriented in the same direction, and that direction is different from the direction in which the pressure-sensitive surface of the first sensor 21a is oriented, and (ii) the directions in which the pressure-sensitive surface of the first sensor 21a and the pressure-sensitive surfaces of the four second sensors 21b are oriented are the directions in which a subject pressurizes the pressure-sensitive surface of the first sensor 21a, and the pressure-sensitive surfaces of the four second sensors 21b such that the gripping force measurement device 1 is grippable by the subject. The "grippable" described herein means that the gripping force measurement device 1 can be lifted and maintained in place by pressurizing to sandwich the first sensor 21a and the second sensors 21b with fingers or the like as described above.

Note that in the above (i), the pressure-sensitive surfaces of the four second sensors 21b are oriented in the same direction, but these pressure-sensitive surfaces may not be oriented in completely the same direction. Specifically, in the case where the first sensor 21a is pressurized with a thumb, as long as the other four fingers can pressurize the second sensors 21b to grip the gripping force measurement device 1, the direction of the pressure-sensitive surfaces can be adjusted as appropriate.

Additionally, in the present embodiment, the pressure-sensitive surface of the pressure sensor 21 is planar, but may be curved. It is sufficient that in at least any region of each pressure-sensitive surface, the microscopic direction of the pressure-sensitive surface satisfies (i) and (ii) described above.

A slit 31a is provided in the first surface 31. As illustrated in FIGS. 3A and 3C, the columnar portion 41b of the button 41 is disposed within the slit 31a. Additionally, the disc-shaped portion 41a and the contact portion 41c are larger than the slit 31a. Thus, the button 41 is movable within the slit 31a in a first axial direction that is a length direction of the slit 31a.

A slit 32a is provided in the second surface 32. The slit 32a and the slit 31a have the lengths in the same direction. The button 41 is movable within the slit 32a in the first axial direction.

The first sensor 21a and the second sensors 21b are fixed to respective corresponding buttons 41. Additionally, the first sensor 21a and the second sensors 21b are slidable in an installation surface 52 in which the first sensor 21a is installed. Thus, the first sensor 21a and the second sensors 21b move with movement of the buttons 41 within the slits 31a, 32a to change positions at which the first sensor 21a and the second sensors 21b are held by the body portion 11.

For example, the second sensors 21b are freely movable as illustrated in FIGS. 4A to 4D. Of course, the first sensor 21a is also freely movable within the slit 31a.

Figure 5A:
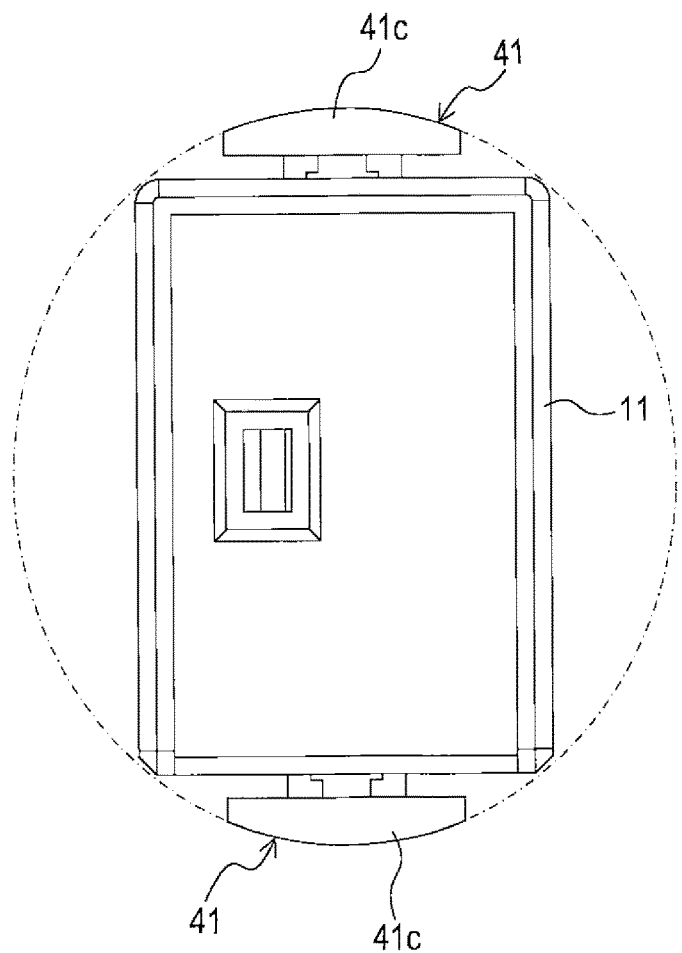
FIG. 5A is an explanatory view of a shape of a contact portion of a button.
Figure 5B:
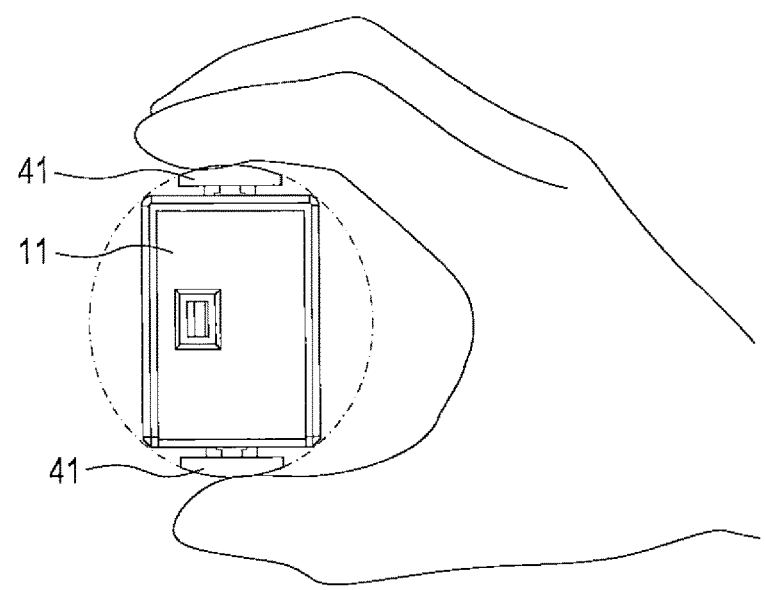
FIG. 5B is a view illustrating a gripping force measurement device gripped by a subject's hand.

As illustrated in FIGS. 5A and 5B, the button 41 for pressurizing the pressure-sensitive surface of the first sensor 21a and the buttons 41 for pressurizing the pressure-sensitive surfaces of the second sensors 21b are disposed at positions at which the buttons 41 protrude outward from the body portion 11. Surfaces of the contact portion 41c of the button 41 on the side of the first surface 31 and the contact portion 41c of the button 41 on the side of the second surface 32 in the protruding direction (in other words, in a direction away from the body portion 11) are located on an arc of the same ellipse. Additionally, the body portion 11 is located inside the ellipse.

1-4. Internal Configuration of Gripping Force Measurement Device

Figure 6:
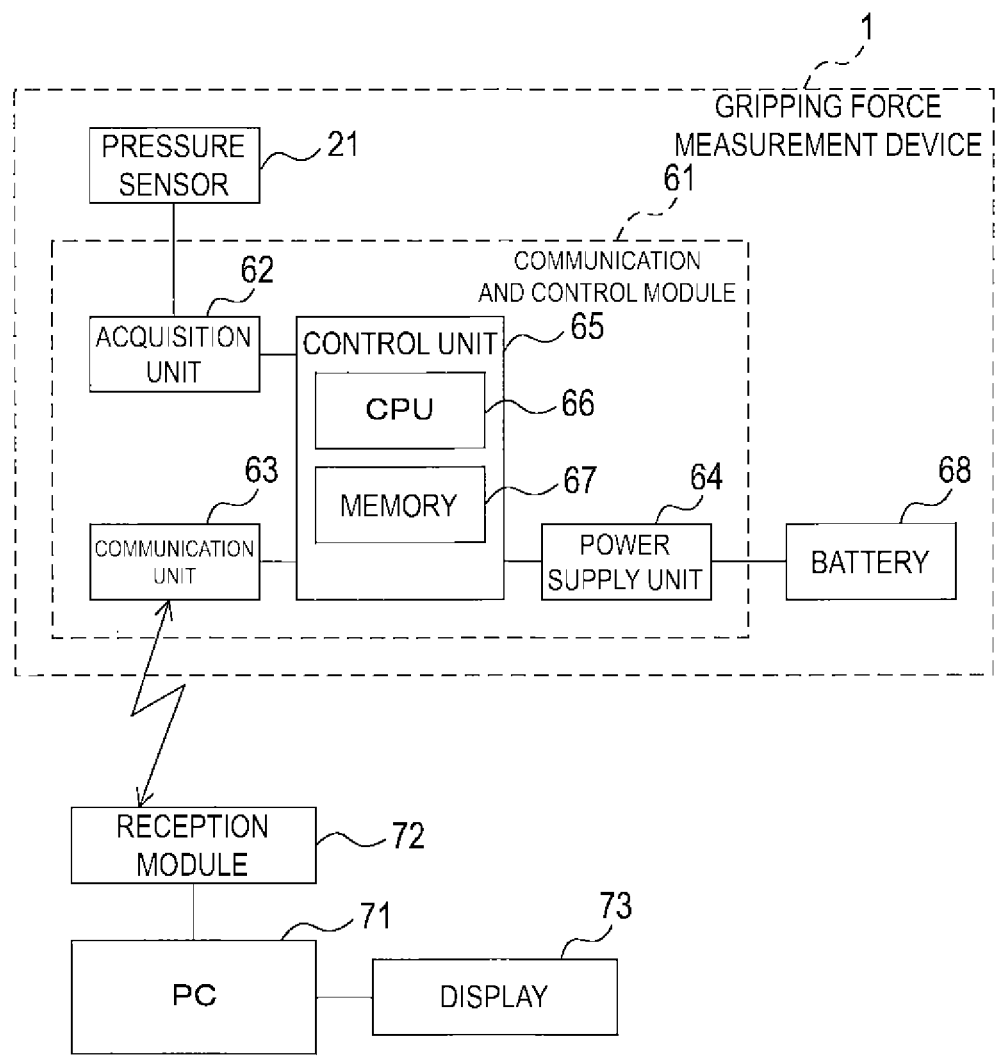
FIG. 6 is a block diagram illustrating the gripping force measurement device in accordance with the first embodiment.

As illustrated in FIG. 6, the gripping force measurement device 1 includes, in addition to the pressure sensor 21, the control and communication module 61 and the battery 68.

The control and communication module 61 includes an acquisition unit 62, a communication unit 63, a power supply unit 64, and a control unit 65.

The acquisition unit 62 is an A/D converter circuit that converts an analog signal that is an output signal of the pressure sensor 21, into a digital signal. The output signal of the pressure sensor 21 refers to a signal that changes in response to the electrical resistance value described above.

The communication unit 63 wirelessly communicates with a reception module 72 connected to a computer system (hereinafter, a PC 71) external to the gripping force measurement device 1. The PC 71 acquires a signal corresponding to the electrical resistance value from the reception module 72, performs necessary processing, and causes a display 73 to display the processing result.

The power supply unit 64 is connected to the battery 68 that supplies power, and supplies power to each unit of the control and communication module 61.

The control unit 65 includes a microcomputer including a CPU 66 and a semiconductor memory (hereinafter, a memory 67) such as a RAM, a ROM, and a flash memory. Various functions of the control unit 65 are realized by causing the CPU 66 to execute a program stored in a non-transient tangible recording medium. In this example, the memory 67 corresponds to the non-transient tangible recording medium that stores the program.

1-5. Processing by CPU

Figure 7:
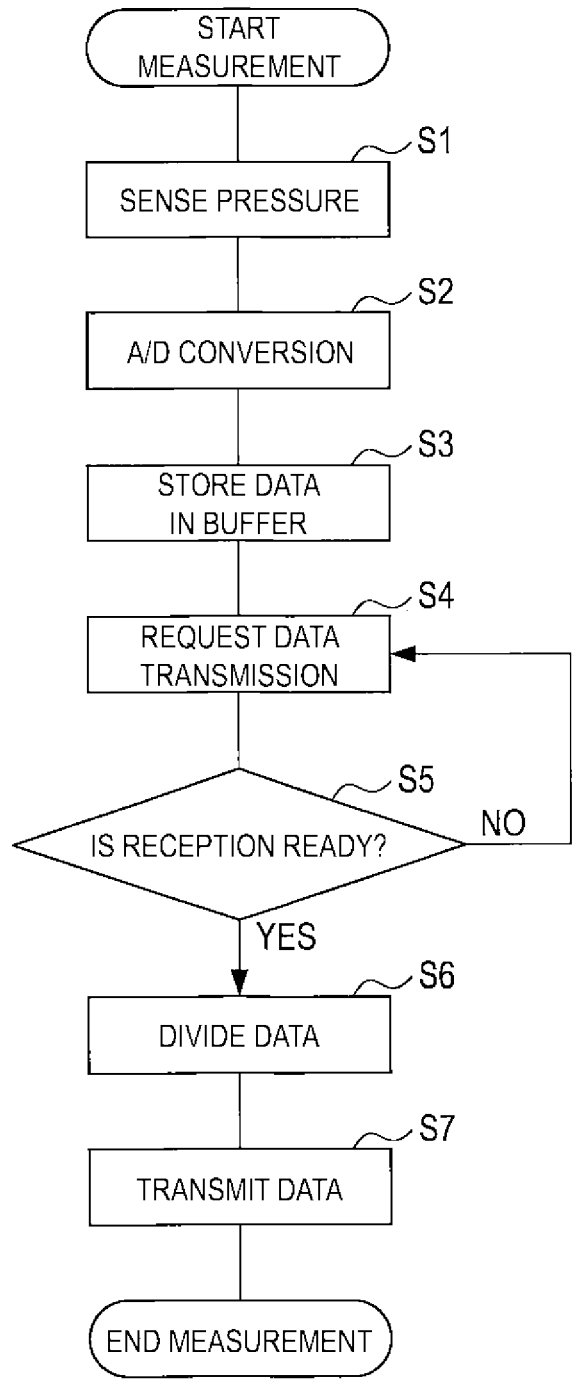
FIG. 7 is a flowchart of measurement processing executed by the gripping force measurement device in accordance with the first embodiment.
Figure 8A:
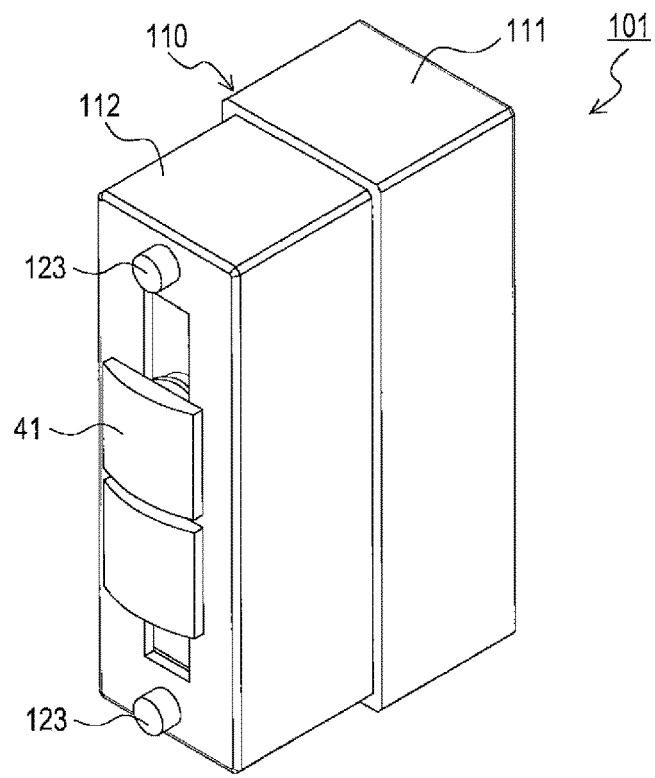
FIG. 8A is a perspective view illustrating a gripping force measurement device in accordance with a second embodiment.
Figure 8B:
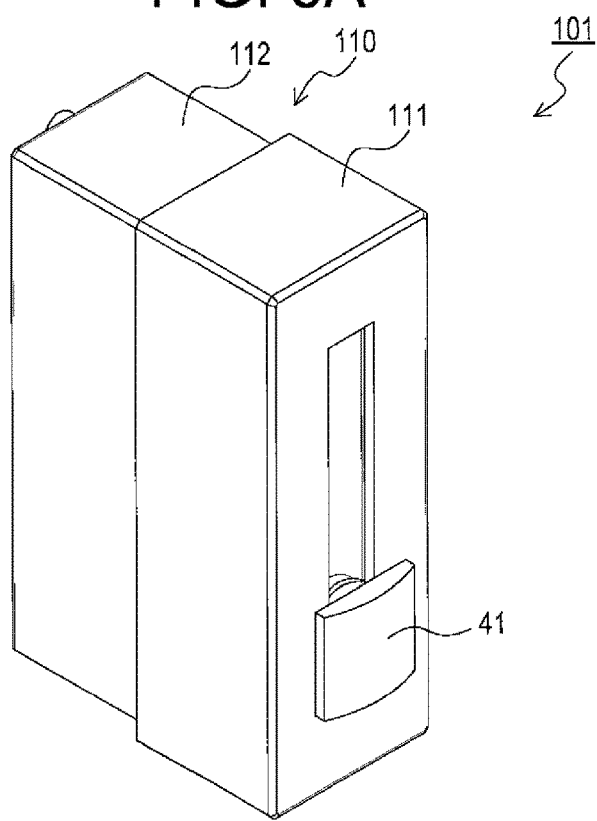
FIG. 8B is a perspective view illustrating the gripping force measurement device from a perspective that is different from that of FIG. 8A.

Next, measurement processing executed by the gripping force measurement device 1 will be described with reference to a flowchart in FIG. 7. The processing starts, for example, when the power button 42 is operated.

First, at S1, the pressure sensor 21 senses pressure applied to the pressure-sensitive surface. An electrical signal corresponding to the pressure is output from the pressure sensor 21.

At S2, the acquisition unit 62 acquires an analog signal from the pressure sensor 21, converts the analog signal into a digital signal, and transmits the digital signal to the control unit 65 as digital data.

At S3, the control unit 65 stores the digital data transmitted from the acquisition unit 62 in a data recording buffer formed in the memory 67, as data of the signal acquired from the pressure sensor 21.

At S4, the control unit 65 requests the PC 71 to transmit data via the communication unit 63.

At S5, the control unit 65 receives a response from the PC 71 to determine whether or not reception is ready. When reception is not ready, or no response is made, the processing returns to S4. When reception is ready, the processing proceeds to S6.

At S6, the control unit 65 divides the data stored at S3 by 8 bits.

At S7, the control unit 65 sequentially transmits the data divided at S6 to the PC 71 via the communication unit 63. After S7, the measurement processing ends.

Note that, when the request to transmit data is received at S4, the PC 71 transmits a message indicating that the request can be received to the gripping force measurement device 1 when the request is receivable. Subsequently, the PC 71 receives the data transmitted at S7 and recombines the divided data. Then, the PC 71 calculates a pressure value based on the recombined data, and causes the display to display the calculation result.

1-6. Effects

The following effects are obtained according to the first embodiment described above.

(1a) In the gripping force measurement device 1, a thumb is brought into contact with the first sensor 21a and fingers other than the thumb are brought into contact with the four second sensors 21b, respectively to apply a force to sandwich the sensors. Accordingly, the gripping force measurement device 1 can acquire more detailed information on finger force, as compared to the case of measuring gripping force of the whole hand.

(1b) Since the positions of the pressure sensors 21 and the buttons 41 can be changed in the gripping force measurement device 1, the positions of the pressure-sensitive surfaces of the pressure sensors 21 can be changed to match a hand (or position of fingers) of a subject. Accordingly, a subject can appropriately pressurize the buttons 41 to appropriately measure force.

(1c) Since the buttons 41 protrude from the body portion 11 in the gripping force measurement device 1, as illustrated in FIG. 5B, fingers are less likely to come into contact with the body portion 11 when the buttons 41 are operated. Accordingly, a risk that finger force is applied to the body portion 11 or that the pressure-sensitive surface of the pressure sensor 21 is pressurized in an improper direction can be reduced, and force measurement can be performed appropriately. Additionally, since the surface of the contact portion 41c follows the arc of the ellipse, a subject can grip the buttons 41 like gripping an elliptical barrel.

2. Second Embodiment 2-1. Differences from First Embodiment

A configuration of a second embodiment is fundamentally the same as the configuration of the first embodiment. Thus, differences will be described mainly and description of configurations that are the same will be omitted. Note that reference numerals in the present embodiment that are the same as those in the first embodiment refer to the same constituents, and reference is made to the preceding description.

FIGS. 8A and 8B and FIGS. 9A to 9D each illustrates a gripping force measurement device 101 in accordance with the second embodiment.

A body portion 110 of the gripping force measurement device 101 in accordance with the second embodiment includes a first housing 111 that holds a first sensor 21a and a second housing 112 that holds second sensors 21b, and further includes a change mechanism 121 that changes the distance between the first housing 111 and the second housing 112.

The change mechanism 121 includes a female screw portion 122 provided in the first housing 111 and a male screw portion 123 provided on the second housing 112.

The female screw portion 122 is a tubular member having a female screw formed inside, and is fixed to the first housing 111. Additionally, the female screw portion 122 is disposed to include an opening at an end in a direction from the first housing 111 toward the second housing 112. In the second embodiment, the direction from the first housing 111 toward the second housing 112 is referred to as a rearward direction.

The male screw portion 123 is provided on the second housing 112 such that the threaded tip is oriented in the opposite direction to the rear direction. Additionally, the male screw portion 123 is rotatable about a longitudinal axis extending in the front-back direction. Additionally, although not illustrated in the drawings, the male screw portion 123 is constituted to be relatively immovable with respect to the second housing 112 in the front-back direction.

Figure 9A:
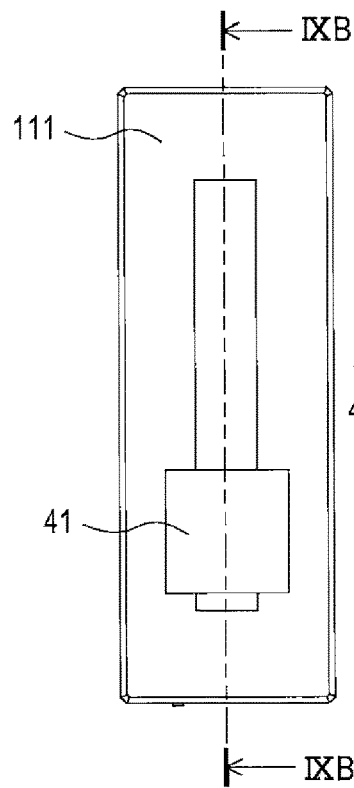
FIG. 9A is a rear view illustrating the gripping force measurement device in accordance with the second embodiment.
Figure 9B:
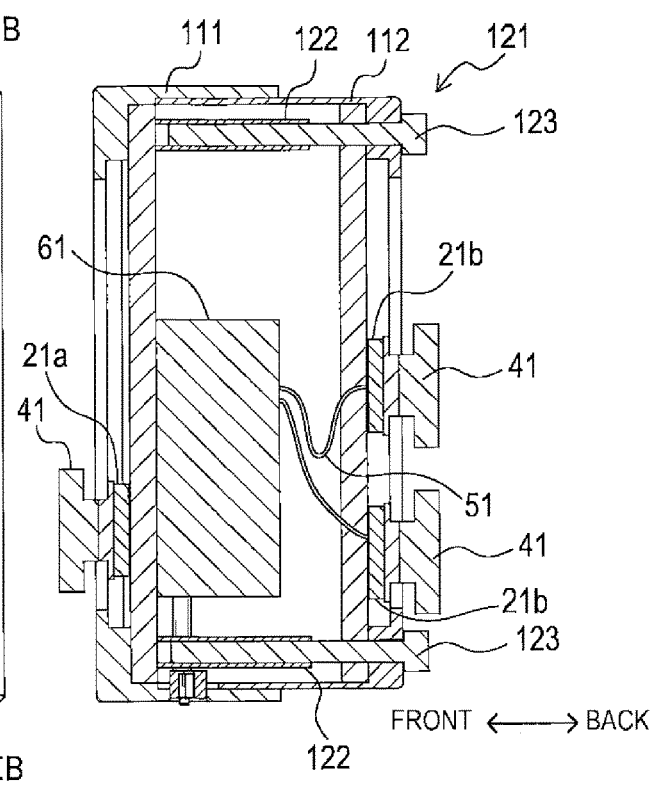
FIG. 9B is a cross-sectional view taken along IXB-IXB in FIG. 9A.
Figure 9C:
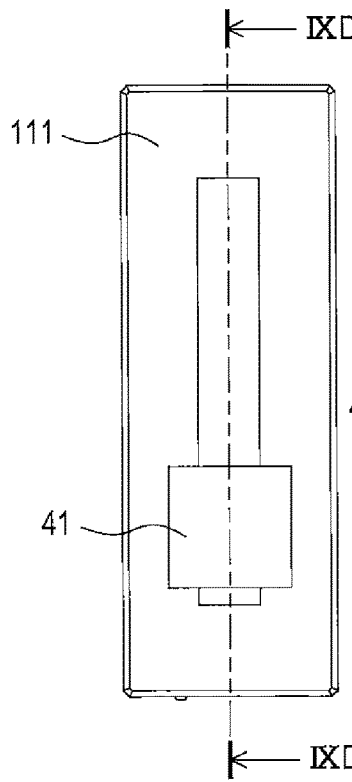
FIG. 9C is a rear view illustrating a state where a body portion of the gripping force measurement device is deformed.
Figure 9D:
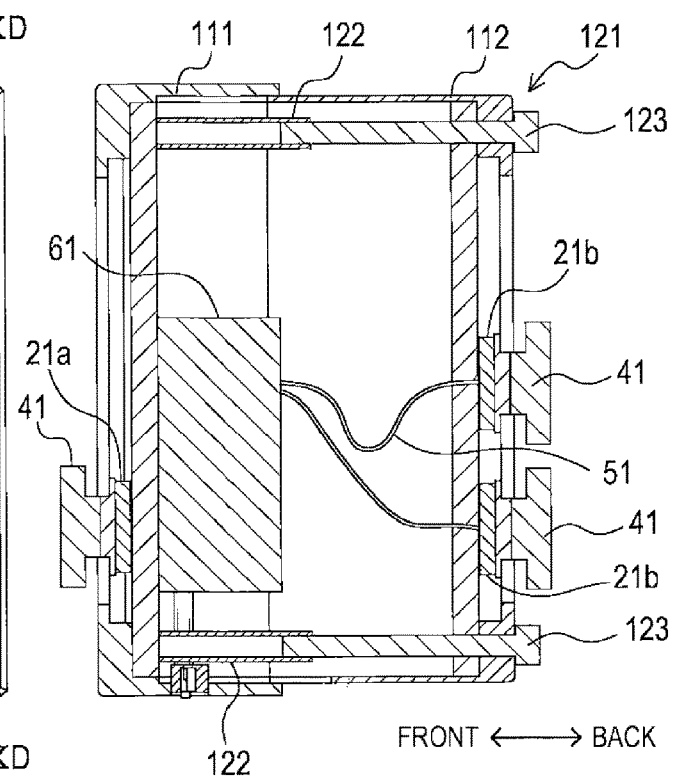
FIG. 9D is a cross-sectional view taken along IXD-IXD in FIG. 9C.

As illustrated in FIGS. 9B, 9D, and the like, the second housing 112 may enter the inside of the first housing 111. Additionally, the male screw portion 123 can be inserted into the female screw portion 122. When the male screw portion 123 is rotated, the female screw portion 122 and the male screw portion 123 are screwed together. Accordingly, the positional relationship in the front-back direction between the first housing 111 and the second housing 112 is determined. Rotation of the male screw portion 123 changes the depth of insertion of the male screw portion 123 into the female screw portion 122. Accordingly, the distance in the front-back direction between the first housing 111 and the second housing 112 changes.

As described above, the first housing 111 is provided with the first sensor 21a, and the second housing 112 is provided with the second sensors 21b. Thus, the body portion 110 can change the distance between a button 41 for pressurizing a pressure-sensitive surface of the first sensor 21a and a buttons 41 for pressurizing pressure-sensitive surfaces of the second sensors 21b. Note that the distance is adjustable in the range of at least 40 to 100 mm.

In the second embodiment, the one first sensor 21a is provided in the first housing 111 and the two second sensors 21b are provided in the second housing 112. However, the two second sensors 21b may be provided in the first housing 111, and the one first sensor 21a may be provided in the second housing 112.

2-2. Effects

In addition to the effects of the first embodiment described above, the following effects are obtained according to the second embodiment.

That is, in the gripping force measurement device 101, the distance between the button 41 for pressurizing the pressure-sensitive surface of the first sensor 21a and the buttons 41 for pressurizing the pressure-sensitive surfaces of the second sensors 21b can be changed according to a subject's hand. Thus, force measurement can be performed appropriately by the gripping force measurement device 101.

3. Other Embodiments

Description of the embodiments of the present disclosure is given above. It is to be understood that the present disclosure is not limited to these embodiments and various forms may be made within the technical scope of the present disclosure.

(3A) In the first embodiment, the one first sensor 21a is disposed in the first surface 31 of the body portion 11 and the four second sensors 21b are disposed in the second surface 32. However, the number of the pressure sensors 21 disposed is not limited to this. It is sufficient that at least one pressure sensor 21 is disposed in the first surface 31, that is, two or more pressure sensors 21 may be provided. Additionally, it is sufficient that at least two pressure sensors 21 are disposed in the second surface 32, and three or more pressure sensors 21 may be provided.

Additionally, in the second embodiment, the one first sensor 21a is provided in the first housing 111 and the two second sensors 21b are provided in the second housing 112. However, two or more first sensors 21a may be provided in the first housing 111, and three or more second sensors 21b may be provided in the second housing 112.

(3B) In the first and second embodiments, the pressure-sensitive surface of the first sensor 21a and the pressure-sensitive surfaces of the second sensors 21b are disposed to be oriented in directly opposite directions. However, as long as the first sensor 21a and the second sensors 21b are disposed to be sandwiched by fingers, the direction in which the pressure-sensitive surfaces are oriented may not be directly opposite directions, and the first sensor 21a and the second sensors 21b may be disposed to be oriented in the inclined direction.

Additionally, the directions in which the pressure-sensitive surfaces of the plurality of second sensors 21b are oriented may not be the same direction, and the pressure-sensitive surfaces of the one or more second sensors 21b may be oriented in a direction different from directions in which the other second sensors 21b are oriented.

Note that, as in the first and second embodiments described above, the button 41 may protrude along the direction in which the pressure-sensitive surface is oriented, or may protrude obliquely from the direction in which the pressure-sensitive surface is oriented.

(3C) In the first and second embodiments, the positions of all of the buttons 41 and the pressure sensors 21 can be changed by sliding. However, positions of only some buttons 41 and some pressure sensors may be changeable, or a position of any of the buttons 41 may not be changeable. For example, only the first sensor 21a that can be used with a thumb and the corresponding button 41 may be slidable, or only the one or more second sensors 21b may be slidable.

(3D) The body portion may be provided with a guide portion that comes into contact with a subject's finger to guide a position of the finger of the subject with respect to the pressure-sensitive surface of at least one of the two or more second sensors 21b.

Figure 10:
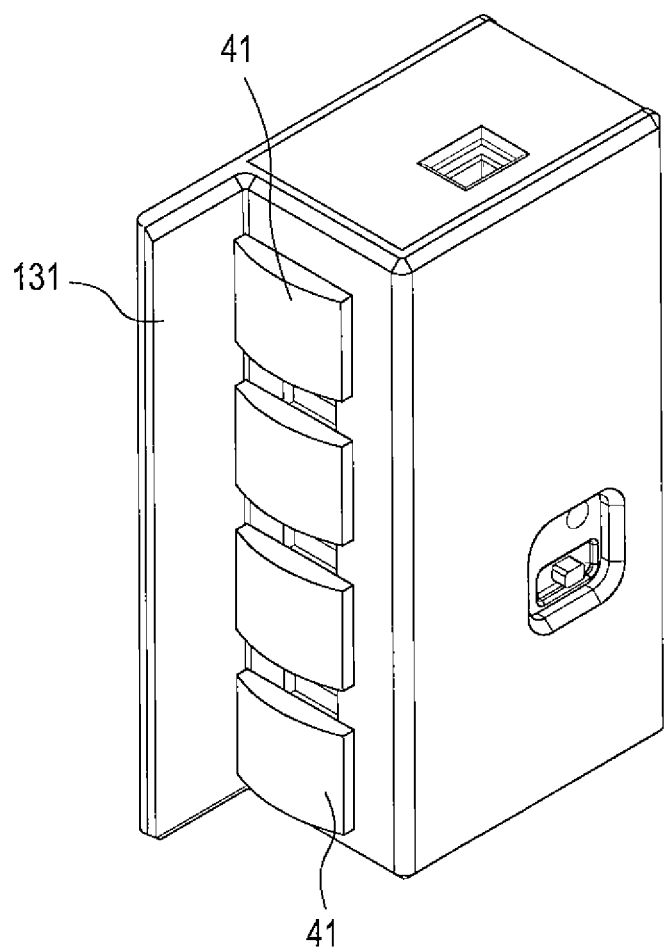
FIG. 10 is a perspective view illustrating a gripping force measurement device in accordance with a modification.

For example, as illustrated in FIG. 10, a guide portion 131 having a plate-like shape can be provided along four buttons 41 corresponding to the second sensors 21b. Finger tips come into contact with the guide portion 131 to roughly determine positions of fingers. Thus, the finger tips can be guided to appropriate positions of the buttons 41.

The shape of the guide portion is not limited to the shape illustrated in FIG. 10, and may have various shapes that can guide the positions of fingers. In addition, it is not necessary to provide the guide portion 131 for all fingers, and the guide portion may be provided only for some fingers.

(3E) In the embodiments described above, the buttons 41 each having the contact portion 41c having a convex shape protrude from the body portion. However, the shapes and arrangement of the buttons 41 are not particularly limited.

For example, a tip of the button 41 may have a planar shape or may be a concave shape depressed at a central portion.

Figure 11A:
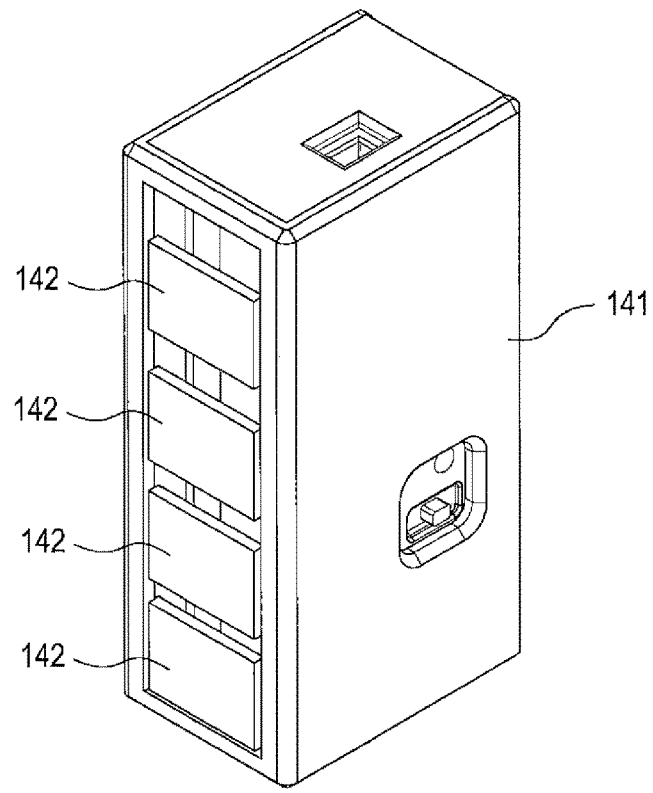
FIG. 11A is a perspective view illustrating a gripping force measurement device in accordance with a modification.
Figure 11B:
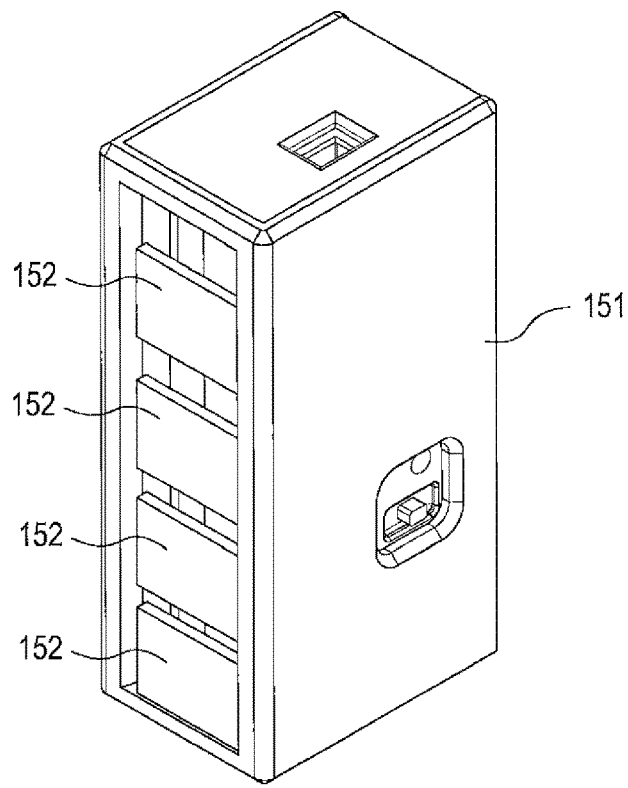
FIG. 11B is a perspective view illustrating a gripping force measurement device in accordance with a modification.

Additionally, as also illustrated FIG. 11A, tip surfaces of buttons 142 each having a planar shape may be flush with an outer surface of a body portion 141. Additionally, as illustrated in FIG. 11B, tip surfaces of buttons 152 may be disposed further inward than an outer surface of a body portion 151.

(3F) The shape of the body portion is not particularly limited as long as the body portion can hold a plurality of pressure sensors. For example, the body portion may have a cylindrical shape. Additionally, the shape of the body portion may be a shape obtained by appropriately combining a rod-shaped body, a tubular body, a block body, and the like.

(3G) In the first and second embodiments described above, the pressure sensor is made from the conductive foam elastomer material and measures pressure based on the electrical resistance that changes by pressurization. However, the pressure sensor that can be used in the gripping force measurement device of the present disclosure may be a sensor other than the sensor described above. For example, a sensor using a comb type electrode may be employed as the pressure sensor. The sensor using a comb-type electrode is a sensor that senses pressure from a change in electrical resistance due to a change in the contact area with a film under pressurization. The sensor may be configured to detect pressure by a change in capacitance made under pressurization. Additionally, a load cell having a Wheatstone bridge circuit may also be used as the pressure sensor.

Figure 12A:
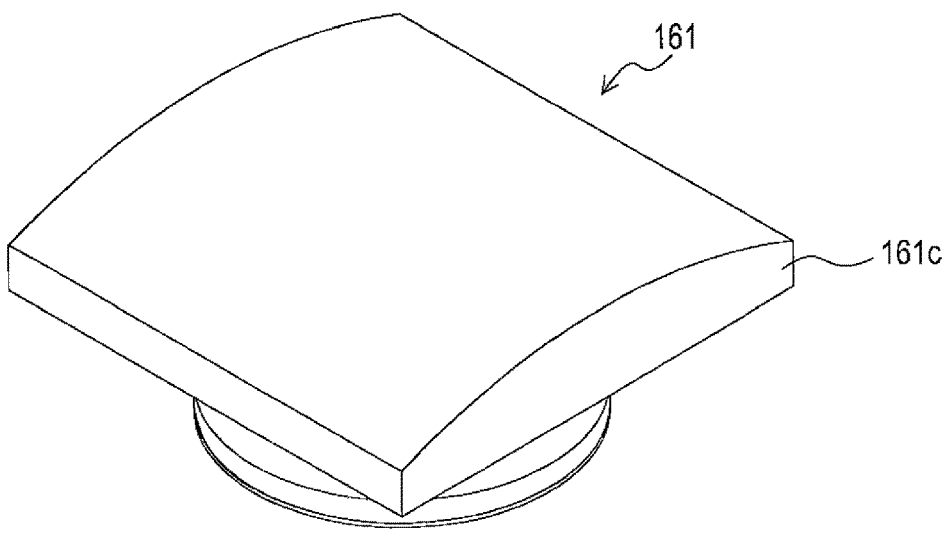
FIG. 12A is a perspective view illustrating a button in accordance with a modification.
Figure 12B:
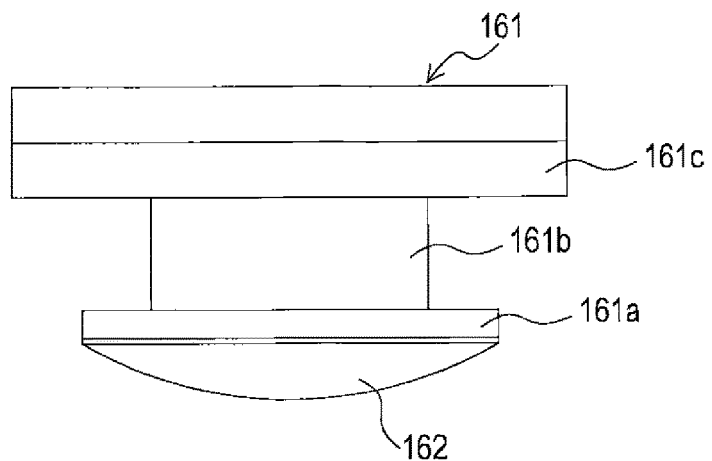
FIG. 12B is a side view illustrating the button in accordance with the modification.
Figure 12C:
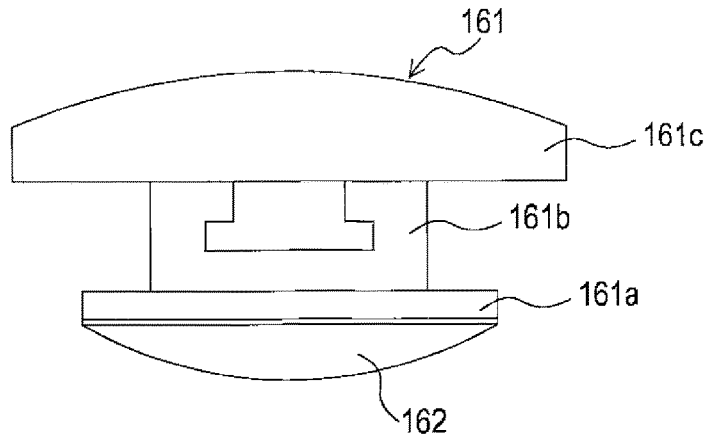
FIG. 12C is a plan view illustrating the button in accordance with the modification.

When a sensor having a small thickness such as the sensor using the comb-type electrode is used, a button 161 as illustrated in FIGS. 12A to 12C can be used. The button 161 includes a disc-shaped portion 161a, a columnar portion 161b, a contact portion 161c, and a contact auxiliary portion 162. The disc-shaped portion 161a, the columnar portion 161b, and the contact portion 161c have the same shapes as the shapes of the disc-shaped portion 41a, the columnar portion 41b, and the contact portion 41c of the button 41 described above. The contact auxiliary portion 162 is a spherical rubber and is provided below the disc-shaped portion 161a.

Figure 13:
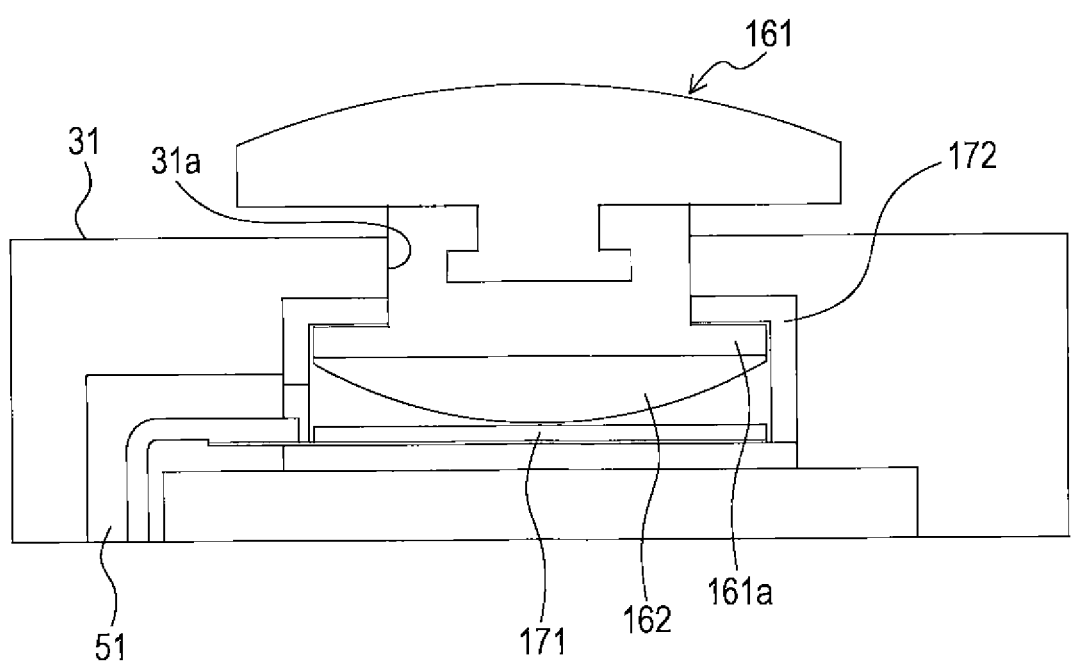
FIG. 13 is a cross-sectional view illustrating a pressure sensor, a button, and a periphery of the button in accordance with a modification.

When such a button 161 is used, a sensor periphery can be configured as illustrated in FIG. 13. The button 161 is disposed such that the contact auxiliary portion 162 is located along a pressure-sensitive surface of a thin pressure sensor 171 using a comb-type electrode. When the button 161 is pressed against the pressure sensor 171, a tip of the contact auxiliary portion 162 pressurizes the pressure sensor 171 and pressure is measured from a change in electric resistance of the comb-type electrode. Since force caused by pressurization concentrates on the tip of the contact auxiliary portion 162, the pressure sensor 171 can suitably measure pressure.

In the example in FIG. 13, a contact surface between the pressure sensor 171 and the contact auxiliary portion 162 is small, and the pressure sensor 171 cannot be fixed to the button 161. Thus, a housing 172 is provided such that the button 161 is in an appropriate position.

Note that the shape of the contact auxiliary portion 162 is not particularly limited. For example, the shape of the contact auxiliary portion 162 may be a cylindrical shape.

The invention claimed is:

1. A gripping force measurement device comprising:
a body portion; and
a plurality of pressure sensors held by the body portion, wherein the plurality of pressure sensors includes a first sensor that is at least one pressure sensor, and two or more second sensors other than the first sensor, the two or more second sensors including pressure-sensitive surfaces oriented in a direction different from the pressure-sensitive surface of the first sensor,
a pressure-sensitive surface of the first sensor and the pressure-sensitive surfaces of the two or more second sensors are disposed such that, when a subject pressurizes the pressure-sensitive surface of the first sensor and the pressure-sensitive surfaces of the two or more second sensors, the gripping force measurement device is grippable by the subject, and
the body portion holds the first sensor slidable in a first specified range, and holds the second sensors slidable in a second specified range.

2. The gripping force measurement device according to claim 1, further comprising a plate-like guide portion provided in the body portion, and configured to come into contact with a fingertips of the subject to guide positions of fingers with respect to the pressure-sensitive surface of at least one of the two or more second sensors.

3. The gripping force measurement device according to claim 1, wherein
the body portion includes a plurality of buttons for pressurizing the plurality of pressure sensors; and
among the plurality of buttons, a button for pressurizing the pressure-sensitive surface of the first sensor and a button for pressurizing at least one of the pressure-sensitive surfaces of the two or more second sensors protrude outward from the body portion.

4. The gripping force measurement device according to claim 2, wherein the body portion includes a plurality of buttons for pressurizing the plurality of pressure sensors; and
among the plurality of buttons, a button for pressurizing the pressure-sensitive surface of the first sensor and a button for pressurizing at least one of the pressure-sensitive surfaces of the two or more second sensors protrude outward from the body portion.

5. The gripping force measurement device according to claim 1, wherein
the body portion is configured such that a distance between the first sensor and the two or more second sensors is changeable.

6. The gripping force measurement device according to claim 2, wherein the body portion is configured such that a distance between the first sensor and the two or more second sensors is changeable.

7. The gripping force measurement device according to claim 3, wherein the body portion is configured such that a distance between the first sensor and the two or more second sensors is changeable.

8. The gripping force measurement device according to claim 4, wherein
the body portion is configured such that a distance between the first sensor and the two or more second sensors is changeable.

* * * * *